US009211226B1

(12) United States Patent
Menzel

(10) Patent No.: US 9,211,226 B1
(45) Date of Patent: Dec. 15, 2015

(54) INELASTIC SELF-ADJUSTING GRADUATED STOCKING FOR THE TREATMENT OF VENOUS STASIS DISEASE

(71) Applicant: Thomas E. Menzel, Tomah, WI (US)

(72) Inventor: Thomas E. Menzel, Tomah, WI (US)

( * ) Notice: Subject to any disclaimer, the term of this patent is extended or adjusted under 35 U.S.C. 154(b) by 504 days.

(21) Appl. No.: 13/833,447

(22) Filed: Mar. 15, 2013

Related U.S. Application Data

(60) Provisional application No. 61/638,597, filed on Apr. 26, 2012.

(51) Int. Cl.
*A61M 11/00* (2006.01)
*A61H 9/00* (2006.01)

(52) U.S. Cl.
CPC ........................................ *A61H 9/00* (2013.01)

(58) Field of Classification Search
CPC ........... A61H 7/00; A61H 7/007; A61H 9/00; A61H 9/0007; A61H 9/005; A61H 9/0078; A61H 9/0092; A61H 15/00; A61H 15/0078; A61H 2201/0103; A61H 2201/0134; A61H 2201/0157; A61H 2201/1207; A61H 2201/1664; A61H 2201/1654; A61H 2205/00; A61H 2205/10; A61H 2209/00
USPC ..................................... 601/148–152; 602/13
See application file for complete search history.

(56) References Cited

U.S. PATENT DOCUMENTS

| | | | | |
|---|---|---|---|---|
| 4,153,050 | A | 5/1979 | Bishop et al. | |
| 5,022,387 | A | 6/1991 | Hasty | |
| 5,218,954 | A * | 6/1993 | van Bemmelen | 601/151 |
| 5,310,400 | A * | 5/1994 | Rogers et al. | 602/5 |
| 5,546,955 | A | 8/1996 | Wilk | |
| 5,711,760 | A * | 1/1998 | Ibrahim et al. | 601/149 |
| 5,843,007 | A | 12/1998 | McEwen et al. | |
| 5,891,065 | A | 4/1999 | Cariapa et al. | |
| 6,123,681 | A | 9/2000 | Brown, III | |
| 6,129,688 | A | 10/2000 | Arkans | |
| 6,216,495 | B1 | 4/2001 | Couzan et al. | |
| 7,637,879 | B2 | 12/2009 | Barak et al. | |
| 8,394,042 | B1 * | 3/2013 | Mirza | 601/150 |
| 2003/0045821 | A1 | 3/2003 | Iker | |
| 2004/0010212 | A1 | 1/2004 | Kuiper et al. | |
| 2006/0036203 | A1 * | 2/2006 | Ouchene et al. | 601/151 |
| 2007/0179416 | A1 | 8/2007 | Obrien et al. | |
| 2007/0179421 | A1 * | 8/2007 | Farrow | 602/75 |
| 2009/0234265 | A1 | 9/2009 | Reid, Jr. et al. | |
| 2013/0085428 | A1 * | 4/2013 | Deshpande | 601/148 |

* cited by examiner

*Primary Examiner* — Steven Douglas
(74) *Attorney, Agent, or Firm* — Charles S. Sara, Esq.; DeWitt Ross & Stevens SC

(57) ABSTRACT

A garment for the treatment of venous stasis disease is directed to an inelastic self-adjusting graduated stocking which includes the stocking, a closure device and a fluid bladder. The stocking is comprised of an interior non-elastic mesh, preferably made of nylon.

20 Claims, 4 Drawing Sheets

INELASTIC SELF-ADJUSTING GRADUATED STOCKING FOR THE TREATMENT OF VENOUS STASIS DISEASE

CROSS-REFERENCE TO RELATED APPLICATION

The application claims priority to U.S. Provisional Application entitled "INELASTIC SELF-ADJUSTING GRADUATED STOCKING FOR THE TREATMENT OF VENOUS STASIS DISEASE," serial number 60/61/638,597, filed Apr. 26, 2012, which is incorporated herein by reference in its entirety.

FIELD OF THE INVENTION

The present invention is directed to a garment for the treatment of venous stasis disease and varicosities.

BACKGROUND

Venous compression garments have long been the mainstay of treatment for venous stasis disease and varicosities. Prior art references show a variety of types of stockings or body coverings, specifically leg coverings, for the treatment of venous stasis disease and/or deep vein thrombosis. For example, U.S. Patent Publication 2009/0234265 to Reid, Jr., et al. is directed to a stocking made of a compression adjustable fabric, which can include an inflatable tube. The stocking may or may not have expansion properties. U.S. Patent Publication 2004/0010212 to Kuiper et al. is directed to a limb covering for treating swelling and other problems of the limb. This device includes a covering which uses hydrostatic pressure applied to the limb to treat chronic swelling. The covering includes a flexible substantially non-distensible outer layer which is drawn to a flexible, distensible inner layer. Between the two layers is a bladder filled with liquid, such as water, to create the hydrostatic pressure applied to the limb when the covering is worn. U.S. Pat. No. 7,637,879 to Barak et al. is directed to a compression sleeve for enveloping a limb and a system for applying pneumatic pressure to the limb.

Although venous compression garments have been shown to be efficacious in the treatment of venous stasis disease, their use is not always successful due to patient or stocking wearer's noncompliance with wearing the garment. The stockings are hard to get on especially for the elderly. They are uncomfortable, and, in the higher compression garments such as needed for treatment of venous stasis ulcers, they can cause pain from ischemia when the legs are raised. In addition, they are just not fashionable. They are uncomfortable in the summer because they are hot. They are expensive, and they become soiled, requiring laundering. With time, the elasticity wears out requiring them to be replaced on a regular basis for them to remain effective.

SUMMARY OF THE INVENTION

The present invention is directed to a garment for the treatment of venous stasis disease that uses a unique and new method of applying pressure that not only creates a pressure gradient to the leg, but also unloads the pressure with elevation. Additionally, it offers the advantage of being rigid and may augment the venous pump.

The device of the present invention is an inelastic self-adjusting graduated stocking for the treatment of venous stasis disease. The stocking includes two basic structures: (1) a stocking and (2) a fluid bladder, part of which encircles the upper thigh and part which extends along the leg. The stocking is made of a generally inelastic nylon mesh or knit fabric. Because the mesh is preferably formed on a bias, it offers some stretch. However, it is not considered a compression stocking.

If desired, the stocking preferably also includes a closure device, such as a zipper, lacing, hook and loop, i.e., VELCRO, fasteners, snaps, or a combination of these; The closure device is typically located in the front of the stocking to enable the stocking to be fitted to the leg with ease. It is also within the scope of the present invention to provide the closure device at other locations of the stocking, such as the back and sides.

The fluid bladder basically comprises a circular reservoir encircling the upper portion of the stocking near the thigh and a bladder column attached to the circular reservoir and extending downwardly along the leg to the ankle area. While the bladder column is preferably located in the posterior region of the leg, it is within the scope of the present invention to locate it in the anterior, i.e., front, or medially, i.e., either side, of the leg. The bladder column extends along the posterior of the leg from the thigh to the ankle area. The bladder is typically filled with a fluid, such as water.

The fluid pressure emanating from the bladder column as it fills transmits circumferentially around the leg by means of the inelastic fabric material. This creates a proper pressure gradient at all levels of the leg from the thigh area to the ankle area. When the wearer lies down or elevates his/her foot, the fluid pressure is automatically relieved from the stocking with the fluid flowing back to the circular reservoir. This action prevents ischemia and pain, which can be experienced typically with current compression devices.

The advantages of the present invention are several. First, the present invention provides a unique and new method of applying gradient pressure to the leg. In addition, this pressure is unloaded with elevation. Further, as the stocking material is not elastic, the stocking should not wear out with laundering. The material, by its nature, will also resist soiling. The stocking should be cool in the summer and relatively inexpensive to construct. As the mesh or knit can be made quite light, it should also be fashionably acceptable, while still allowing for evaporation and cooling during the summer. The entire stocking with fluid can be constructed to be light in weight without encumbering tube, controls, batteries etc. such that the wearer can be mobile.

The concept of incorporating a gravity-fed column of fluid attached to a stocking which is comprised of a non-elastic material, wherein the bladder column of fluid provides an overall pressure gradient to the leg without the requirement for complex controls associated with the garment is a believed to be a novel feature of the present invention.

Further still, the compression stocking of the present invention addresses a serious problem with current, prior art compression devices, i.e., the area behind the medial and lateral prominences (malleolus) at the ankle. This is an area particularly prone to venous stasis ulcers. Due to the concavity of the area, it is very difficult to apply pressure at this area. An advantage of the compression stocking of the present invention is that the bladder column can be extended over this area to apply the proper pressure.

The objects and advantages of the invention will appear more fully from the following detailed description of the preferred embodiment of the invention made in conjunction with the accompanying drawings.

DETAILED DESCRIPTION OF THE INVENTION

Figure 1:
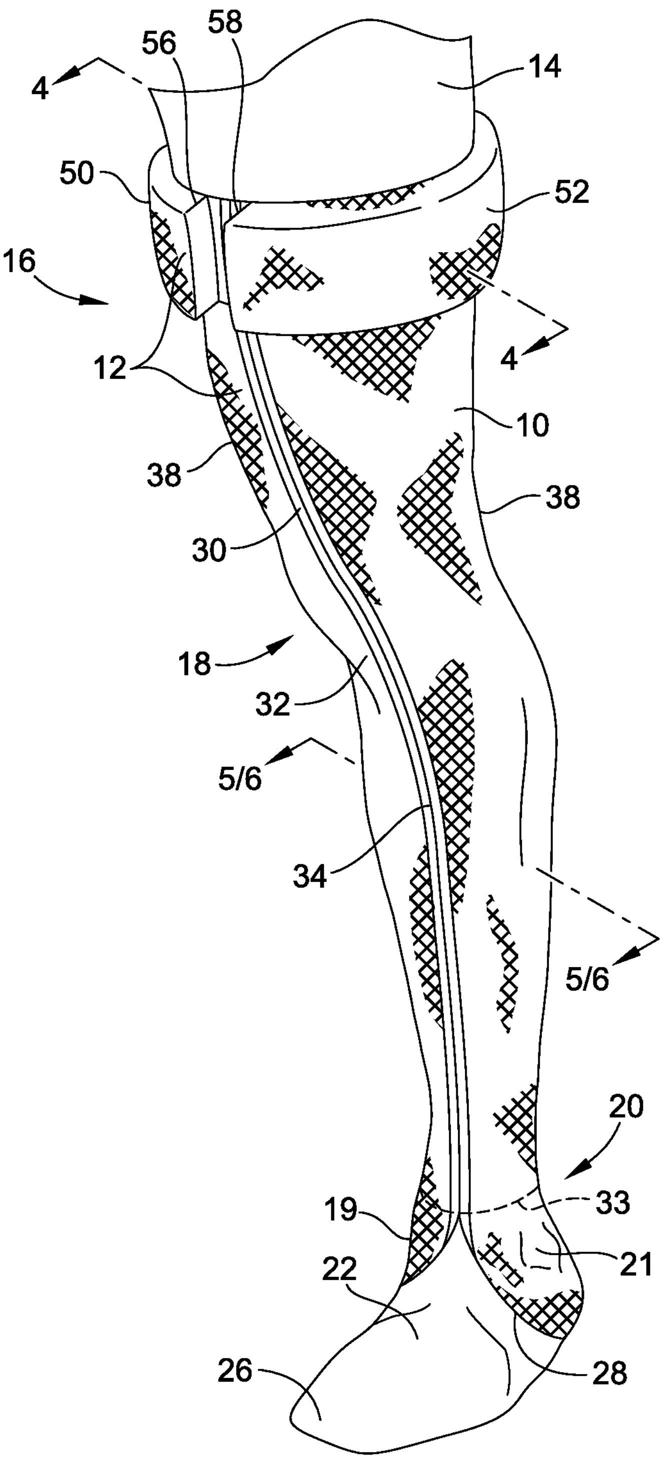
FIG. 1 is a front perspective view of the compression stocking 10 of the present invention on a human leg 14.

Reference is now made to FIG. 1 for the compression stocking 10 of the present invention. The compression stocking 10 is preferably made of a woven material which is generally inelastic when pulled or stretched in the direction of its warp and weft threads. Thus, the term "inelastic," as used in this disclosure, conveys a woven material which is not designed to stretch or expand when pulled along the direction of its warp and weft threads, but does offer some minimal stretch as the fabric mesh is positioned on a bias, i.e., at approximately 45 degrees to its warp and weft threads, as illustrated by cross-hatch lines 12, rather than the strands being placed circumferentially and longitudinally, i.e., in the direction of the warp and weft thread pattern of the material, or by use of a nylon knit. Thus, the material is relatively inelastic circumferentially. As the fabric mesh of the compression stocking 10 can be made of quite light material, it should be acceptable and comfortable for wear. In addition, it should allow for evaporation and cooling of the leg 14.

Figure 2:
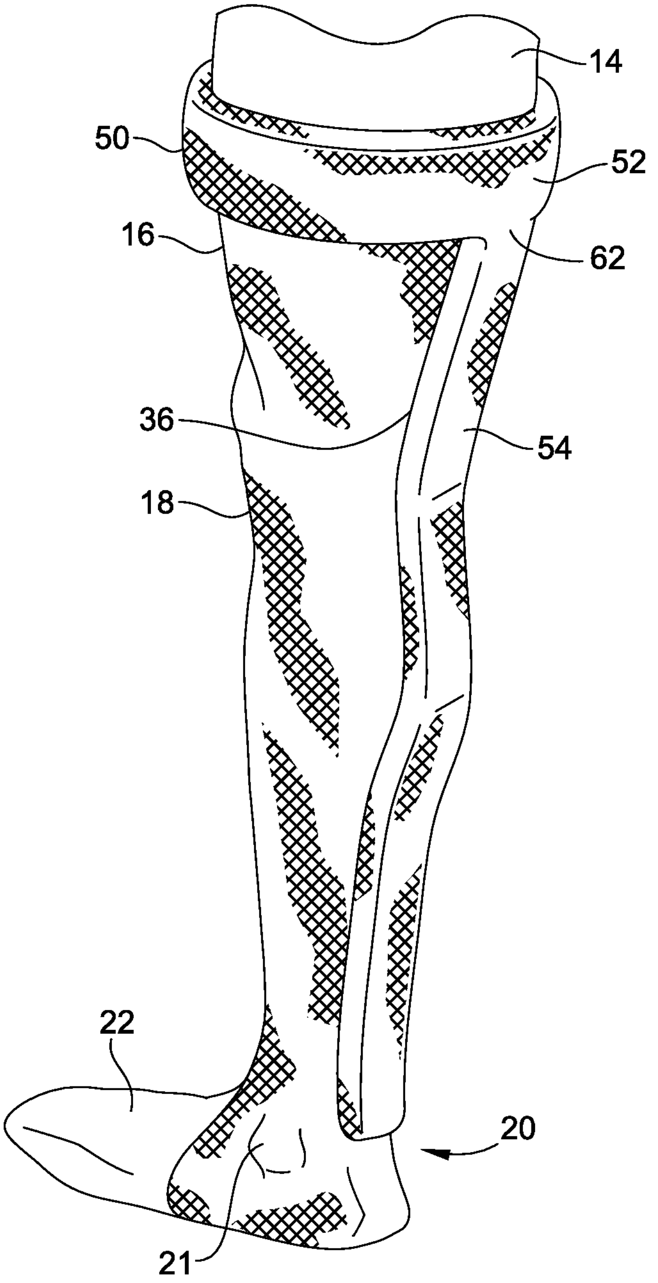
FIG. 2 is a rear perspective view of the compression stocking 10 of the present invention on a human leg 14.
Figure 3:
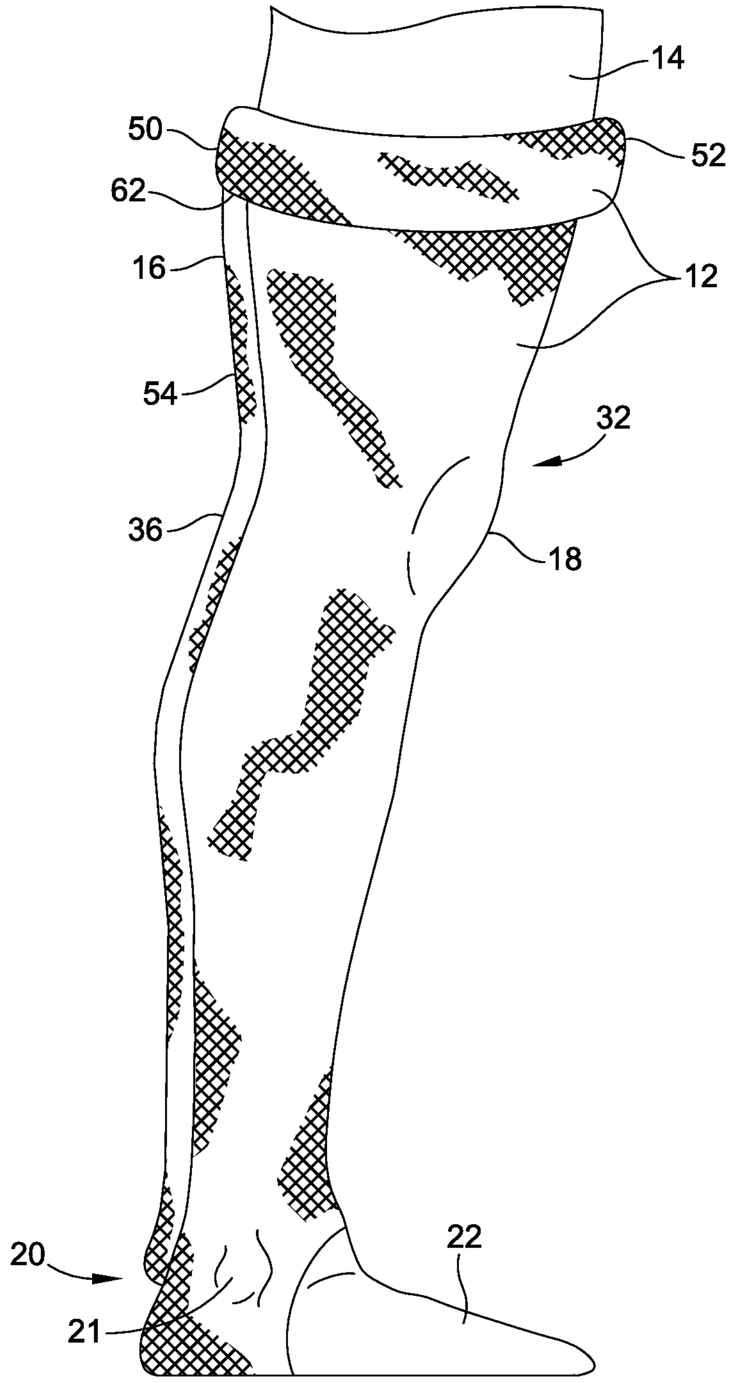
FIG. 3 is a side view of the compression stocking 10 of the present invention on a human leg 14.

The compression stocking 10 is fitted to the leg 14 having an upper or thigh area 16, a middle or knee area 18, a lower or ankle area 20, which includes medial malleolus (or prominence) 19 and a lateral malleolus 21, and a foot 22 with a heel 24 and toe area 26. As illustrated in FIGS. 1-3, the compression stocking 10 includes an opening 28 at the ankle area 20, which covers the heel 24, but not the toe area 26. While this is the preferred compression stocking 10 of the present invention, it is also within the scope of the present invention to having the compression stocking 10 opening 28 end at the ankle area 20, as illustrated by phantom line 33, or completely envelope the toe area 26 (not illustrated).

The compression stocking 10 is fitted to the leg 14 by means of a closure device 30 preferably extending from the thigh area 16 to the ankle area 20 in the front or anterior position 32 of the compression stocking 10. The closure device 30 can be in the form of a hook and loop, i.e., VELCRO, fastener 34, as illustrated in FIG. 1, or alternatively a zipper, lacing, snaps, a combination of these, or other means known to the art. While the preferred location for the closure device 30 is in the front 32 of the compression stocking 10, as illustrated in FIG. 1, it is also within the scope of the invention to place the closure device 30 on the compression stocking 10 at the location of the back or posterior position 36 of the leg 14 or on either side 38 of the compression stocking 10. The closure device 30 also includes a strip of material, preferably elastic material, called a closure guard 31, illustrated in FIGS. 5 and 6.

Figure 4:
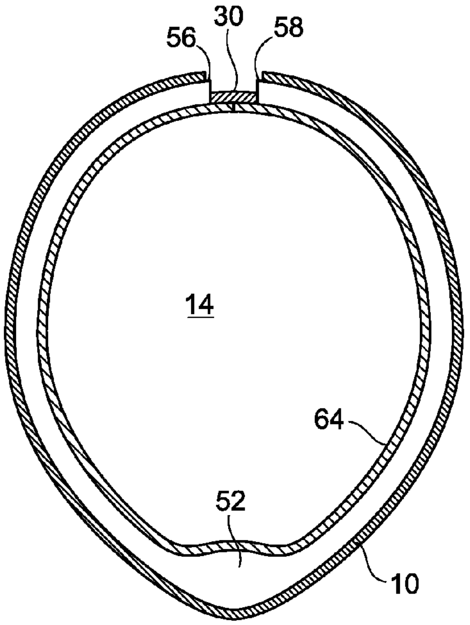
FIG. 4 is cross-sectional view of the compression stocking 10 of the present invention taken at lines 4-4 on FIG. 1.
Figure 5:
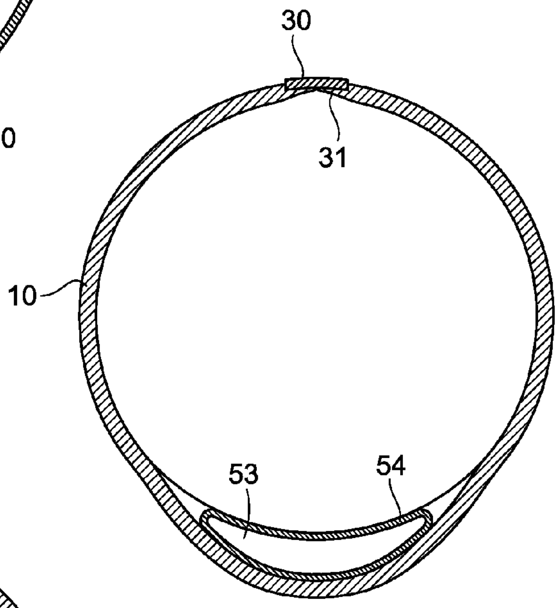
FIG. 5 is a cross-sectional view of the compression stocking 10 of the present invention taken at lines 5/6-5/6 on FIG. 1 illustrating a fluid-inflated bladder column 54.
Figure 6:
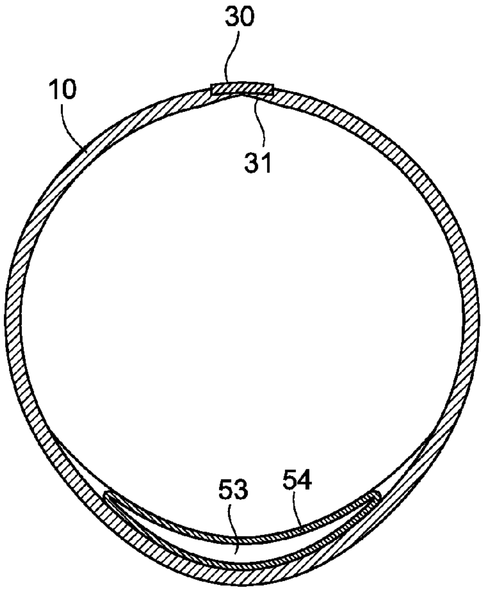
FIG. 6 is a cross-sectional view of the compression stocking 10 of the present invention taken at lines 5/6-5/6 on FIG. 1 illustrating a fluid-deflated bladder column 54.

Attached the interior of the compression stocking 10, illustrated best in FIGS. 4-6, is a fluid-filled bladder 50 comprising a circular reservoir 52 encircling the upper thigh area 16 and a downwardly directed bladder column 54 connected to the circular reservoir 52, such that fluid is allowed to freely move in a channel 53 (illustrated in FIG. 5) between the circular reservoir 52 and the bladder column 54. The bladder 50 is attached to the stocking 10 by means known to the art, such as glue or by creating a pouch in the stocking itself for placement of the bladder. Alternatively, the bladder 50 can be releasably attached to the stocking 10 by snaps, hook and loop fasteners or other means known to art, to allow removal of the bladder 50 in order to wash the stocking 10. While the circular reservoir 52 resides outside the stocking 10, the bladder column 54 is designed to be placed between the stocking 10 and the wearer's leg 14.

As illustrated in FIGS. 1 and 4, the circular reservoir 52 is not continuous as it is interrupted by the closure device 30 at the upper thigh area 16 resulting in termination ends 56 and 58. While this is the preferred means for constructing the compression stocking 10 of the present invention, it is also within the scope to provide a compression stocking 10 without a closure device 30. Thus, the compression stocking 10 would be of the slip on variety such that the compression stocking 10 would fit over the foot 22 for placement on the leg 14. In this manner the circular reservoir 52 will have a continuous channel 60.

The circular reservoir 52 is preferably located between an elastic band 64 and the fabric material comprising the compression stocking 10 in the upper thigh area 16, as illustrated in FIGS. 1-3. The elastic band 64 is designed to hold the compression stocking 10 in place on the leg 14 and prevent the compression stocking 10 from wrinkling or falling from the upper thigh area 16 of the leg 14. A non-compressing space, i.e., extra stocking material, is created over the circular reservoir 52 by sewing the fabric material to the elastic band 64, thereby allowing the circular reservoir 52 to fill with fluid without creating any compressive forces on the wearer's leg 14, by stretching the material of the compression stocking 10. Alternatively, the circular reservoir 52 can be placed exterior to the elastic band 64 and the compression stocking 10 material. Other embodiments such as a garter belt closure mechanism can also be used to hold the compression stocking 10 to the leg 14.

The bladder column 54 connects to the circular reservoir at an intersection 62 and extends the length of the leg 14 to the ankle area 20, as illustrated in FIGS. 2 and 3. The channels 53 and 60 in the bladder 50 preferably contains approximately 100 milliliters (ml) of fluid, although the amount of fluid and/or the dimensions of the bladder 50 can increase or decrease depending on the needs of the wearer. For purposes of the present invention, water will be designated as the preferred fluid. It is within the scope of the present invention to use other fluids, such as oils. The size of the bladder 50 is an estimate and could be made larger or smaller as needed to develop the proper filling and pressure in the compression stocking 10. For example a wider and larger bladder column requires more fluid than a narrower and smaller bladder column 54 to provide the same necessary compression on the leg. For instance, the size of the bladder 50 could be doubled allowing for 4 times the volume. In addition, the currently described bladder 50 could be filled with more than 100 ml of fluid up to between 500 ml and 640 ml. The shape of the bladder column 54 could also be varied along the posterior length 36 of the leg 14 to possibly be wider at the ankle area 20 than at the upper thigh area 16 to allow more volume at the ankle area 20. A widening of the bladder column 54 at the knee area 18 could also be envisioned to allow for flexibility of the compression stocking 10 at the knee area 18.

As stated above and illustrated in FIGS. 2 and 3, the circular reservoir 52 of the bladder 50 is continuous to the bladder column 54 which runs the posterior length 36 of the leg 14 from the upper thigh area 16 to the lower ankle area 20.

Further still, the compression stocking of the present invention addresses a serious problem with current, prior art compression devices, i.e., the area behind the medial and lateral prominences 19, 21 at the ankle. This is an area particularly prone to venous stasis ulcers. Due to the concavity of the area, it is very difficult to apply pressure at this area with current compression devices. An advantage of the compression stocking of the present invention is that the bladder column can be extended over this area to apply the proper pressure.

While the preferred location of the bladder column 54 is on the posterior 36 of the stocking 10, it is within the scope of the invention and, depending on the condition of the wearer, may be advisable to locate the bladder column 54 on the sides 38 of the stocking 10.

In operation, the compression stocking 10 is placed on the wearer's leg 14 and secured by means of the closure device 30 if the compression stocking 10 includes a closure device 30, such as a hook and loop, i.e., VELCRO, fastener 34. Otherwise, the wearer puts on the compression stocking 10 in similar fashion to putting on a standard stocking. When the wearer is in an upright position, i.e., standing or at least partially standing, fluid in the bladder 50 will pass from the circular reservoir 52 to fill the channel 53 of the bladder column 54, illustrated in FIG. 5. The bladder column 54 thus expands which constricts the inelastic fabric of the compression stocking 10 to transmit relieving pressure circumferentially around the leg 14. As the fluid bladder column 54 is a continuous water column, the result is a proper pressure gradient at all levels of the leg 14.

When the wearer lies down, fluid pressure is automatically relieved from the compression stocking 10 with the fluid flowing through the channel 53 back into the circular reservoir 52 channel 60, thus preventing ischemia and pain as experienced with current compression devices.

The garment of the present invention should be relatively inexpensive to construct and, as they are somewhat self-adjusting to size, construction tolerances will not have to be as great as the current garments. The bladder 50 itself can be formed from a plastic sheet cut to an appropriate shape to form the circular reservoir 52 and the bladder column 54, and, sealed along the open edges to form the channel 53 by an appropriate process well-known to the art, such as thermal sealing. Alternatively, the bladder 50 can be formed by taking two sheets of plastic cut to the shape approximating the shape of the bladder illustrated in FIG. 3 and sealing the sheets along all edges according to sealing processes known to the art.

Any version of any component or method step of the invention may be used with any other component or method step of the invention. The elements described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference in their entirety to the same extent as if each individual reference were specifically and individually indicated as being incorporated by reference. In case of conflict between the present disclosure and the incorporated references, the present disclosure controls.

The devices, methods, compounds and compositions of the present invention can comprise, consist of, or consist essentially of the essential elements and limitations described herein, as well as any additional or optional steps, ingredients, components, or limitations described herein or otherwise useful in the art.

While this invention may be embodied in many forms, what is described in detail herein is a specific preferred embodiment of the invention. The present disclosure is an exemplification of the principles of the invention is not intended to limit the invention to the particular embodiments illustrated. It is to be understood that this invention is not limited to the particular examples, process steps, and materials disclosed herein as such process steps and materials may vary somewhat. It is also understood that the terminology used herein is used for the purpose of describing particular embodiments only and is not intended to be limiting since the scope of the present invention will be limited to only the appended claims and equivalents thereof.

What is claimed is:

1. A compression stocking for the treatment of venous stasis disease on a leg having an upper thigh end, a middle knee area and a lower ankle area, as well as anterior, posterior and side positions, comprising:

a. a generally inelastic fabric material in the shape of a stocking having an upper thigh end and a lower foot end;

b. a fluid-containing bladder adapted to be located between the compression stocking and the leg and including:

i. a circular reservoir at the upper thigh end of the fabric material, and ii. a downwardly extending bladder column communicating with the circular reservoir and adapted to extend to the lower ankle area of the leg.

2. The compression stocking of claim 1 further comprising a closure device adapted to secure the compression stocking to the leg.

3. The compression stocking of claim 2, wherein the closure device is selected from the group consisting of zippers, lacing, snaps, buttons, hook and loop fabric, and combinations thereof.

4. The compression stocking of claim 2, wherein the closure device is adapted to be placed at the anterior position of the leg.

5. The compression stocking of claim 2, wherein the closure device is adapted to be placed at the posterior position of the leg.

6. The compression stocking of claim 2, wherein the closure device is adapted to be placed on either side position of the leg.

7. The compression stocking of claim 2 further comprising a closure guard.

8. The compression stocking of claim 1 wherein the fabric material is selected from the group consisting of nylon mesh and knit fabric.

9. The compression stocking of claim 1 wherein the fabric material is adapted to be formed on the leg on a bias.

10. The compression stocking of claim 1 further comprising an elastic band encircling the compression stocking at the upper thigh end of the fabric material and adapted to hold the compression stocking on the leg.

11. The compression stocking of claim 1 wherein the stocking material comprises a non-compressing space encircling the circular reservoir.

12. The compression stocking of claim 1 comprising an opening adapted to be positioned at the lower ankle area.

13. The compression stocking of claim 1 wherein the bladder is releasably attached to the compression stocking.

14. The compression stocking of claim 1, wherein the bladder contains no more than about 500 ml of fluid.

15. The compression stocking of claim 1, wherein the bladder contains water.

16. The compression stocking of claim 1, wherein the bladder is filled with approximately 100 ml of fluid.

17. The compression stocking of claim 1, wherein the bladder column is adapted to be located on the posterior position of the leg.

18. The compression stocking of claim 1, wherein the bladder column is adapted to be located on the anterior position of the leg.

19. The compression stocking of claim 1, wherein the bladder column is adapted to be located on either side position of the leg.

20. A compression stocking for the treatment of venous stasis disease on a leg having an upper thigh end, a middle knee area and a lower ankle area, as well as anterior, posterior and side positions, comprising:

a. an inelastic fabric stocking material in the shape of a stocking having an upper thigh end and a lower foot end;

b. a fluid-containing bladder adapted to be located between the compression stocking and the leg and including:

i. a circular reservoir at the upper thigh end of the fabric material, wherein the stocking material comprises a non-compressing space encircling the circular reservoir, and ii. a downwardly extending bladder column communicating with the circular reservoir and adapted to extend down the posterior position of the leg to the lower ankle area; and c. a closure device adapted to secure the compression stocking to the leg.

* * * * *